United States Patent [19]

Khatri et al.

[11] Patent Number: 4,835,288

[45] Date of Patent: May 30, 1989

[54] PROCESS FOR PREPARING (+)-2,3-DIHYDRO-1H-PYRROLO[1,2-A]PYRROLE-1,7-DICARBOXYLATES

[75] Inventors: Hiralal N. Khatri, Louisville; Michael P. Fleming, Longmont; George C. Schloemer, Lyons, all of Colo.

[73] Assignee: Syntex Inc., Palo Alto, Calif.

[21] Appl. No.: 3,162

[22] Filed: Jan. 14, 1987

[51] Int. Cl.⁴ .............................. C07D 487/04
[52] U.S. Cl. ..................... 548/453; 562/571; 560/171; 548/531
[58] Field of Search ....................... 548/453

[56] References Cited

U.S. PATENT DOCUMENTS

| | | | |
|---|---|---|---|
| 2,708,207 | 5/1955 | Girod | 564/346 |
| 3,752,826 | 8/1973 | Carson | 260/326.3 |
| 4,048,191 | 9/1977 | Carson | 260/326.47 |
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,333,878 | 6/1982 | Dagani | 548/531 |
| 4,344,943 | 8/1982 | Muchowski | 424/245 |
| 4,353,829 | 10/1982 | Thurber et al. | 260/326.25 |
| 4,363,918 | 12/1982 | Albert et al. | 548/531 |
| 4,374,255 | 2/1983 | Kao et al. | 548/531 |
| 4,383,117 | 5/1983 | Kao et al. | 548/531 |
| 4,388,468 | 6/1983 | Dagani | 548/531 |
| 4,455,433 | 6/1984 | Marlett | 548/531 |
| 4,496,741 | 1/1985 | Doherty | 548/453 |
| 4,511,724 | 4/1985 | Chang et al. | 548/452 |
| 4,533,671 | 8/1985 | Biftu et al. | 514/413 |
| 4,536,512 | 8/1985 | Biftu et al. | 514/413 |
| 4,560,699 | 12/1985 | Muchowski et al. | 514/413 |
| 4,565,878 | 1/1986 | Dagani | 548/531 |
| 4,565,879 | 1/1986 | Kao | 548/531 |

FOREIGN PATENT DOCUMENTS

| | | |
|---|---|---|
| 92487 | 10/1983 | European Pat. Off. . |
| 105664 | 4/1984 | European Pat. Off. . |
| 56-154483 | 11/1981 | Japan . |
| 2034304 | 6/1980 | United Kingdom . |

Primary Examiner—David B. Springer
Attorney, Agent, or Firm—Derek P. Freyberg

[57] ABSTRACT

2,3-Dihydro-1H-pyrrolo[1,2-a]pyrrole-1,7-dicarboxylates of the formula,

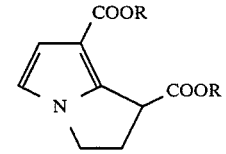

in which each R is independently H or lower alkyl, are prepared from di(lower alkyl) 1,3-acetone-dicarboxylates.

7 Claims, No Drawings

PROCESS FOR PREPARING (+)-2,3-DIHYDRO-1H-PYRROLO[1,2-A]PYRROLE-1,7-DICARBOXYLATES

CROSS-REFERENCE TO RELATED APPLICATION

This application is related to the subject matter of our copending and commonly assigned U.S. patent application Ser. No. 07/003,104, filed January 14, 1987 for "Process for Preparing (±)-2,3-dihydro-1H-pyrrolo[1,2-a]pyrrole-1,7-dicarboxylates", which is incorporated herein by reference.

BACKGROUND OF THE INVENTION

1. Field of the Invention

This invention relates to pyrrolo[1,2-a]pyrroles, and especially to the synthesis of 2,3-dihydro-1H-pyrrolo[1,2-a]pyrrole-1,7-dicarboxylic acid and its dialkyl esters.

2. Background to the Invention

5-Aroyl-2,3-dihydro-1H-pyrrolo[1,2-a]pyrrole-1-carboxylic acids, also known as 5-aroyl-2,3-dihydro-1H-pyrrolizine-1-carboxylic acids, of formula I, and the

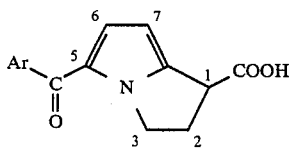

pharmacologically acceptable salts and esters thereof, are useful as analgesic, anti-inflammatory, and antipyretic agents for mammals, including man. They are also smooth muscle relaxants. Two exemplary compounds under clinical study in man are ketorolac, 5-benzoyl-2,3-dihydro-1H-pyrrolo[1,2-a]pyrrole-1carboxylic acid, (I, Ar=C₆H₅), and anirolac, 5-p-anisoyl-2,3-dihydro-1H-pyrrolo[1,2-a]pyrrole-1-carboxylic acid, (I, Ar=p—CH₃O—C₆H₅), both disclosed in U.S. Pat. No. 4,089,969. Other compounds, where the 5-aroyl substituents are substituted or unsubstituted benzoyl, furoyl, thenoyl, and pyrroyl, and where the 6-position on the pyrrolo-pyrrole nucleus is optionally substituted by lower alkyl or halogen, and uses thereof, are also disclosed in a series of patents assigned to Syntex (U.S.A.) Inc., beginning with U.S. Pat. No. 4,089,969, and including U.S. Pat. Nos. 4,087,539; 4,097,579; 4,140,698; 4,232,038; 4,344,943; 4,347,186; 4,458,081; 4,347,187; 4,454,326; 4,347,185; 4,505,927; 4,456,759; 4,353,829; 4,397,862; 4,457,941; and 4,454,151. U.S. Patents Nos. 4,511,724 and 4,536,512, assigned to Merck & Co., Inc., disclose 5-(substituted pyrrol-2-oyl)-2,3-dihydro-1H-pyrrolo-[1,2-a]pyrrole-1-carboxylic acid derivatives and 5-(2,3-dihydro-1H-pyrrolo[1,2-a]pyrrol-2-oyl)-2,3-dihydro-1H-pyrrolo[1,2-a]pyrrole-1-carboxylic acid derivatives, respectively; while U.S. Pat. No. 4,533,671, also assigned to Merck & Co., Inc., discloses 5-(2,3-dihydro-1H-pyrrolo[1,2-a]pyrrol-2-oyl)-2-pyrrole-alkanoic acids and analogs.

Various methods for the preparation of these pyrrolopyrroles are exemplified in the patent and chemical literature, and many proceed through a common intermediate, 2,3-dihydro-1H-pyrrolo[1,2-a]pyrrole-1,7-dicarboxylic acid, (II, R=H), or its dialkyl ester;

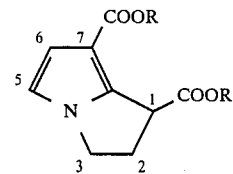

the preparation of which from dimethyl 1,3-acetonedicarboxylate, ethanolamine, and a haloacetaldehyde is disclosed in, for example, U.S. Pat. No. 4,089,969, which is incorporated herein by reference.

The reaction scheme set forth in that patent:

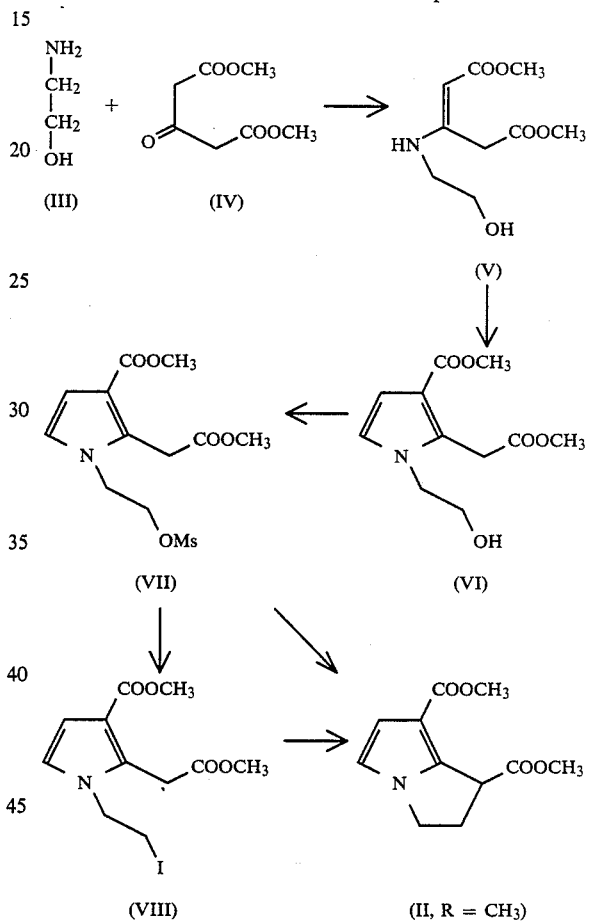

includes the reaction of equimolar amounts of ethanolamine (III) and dimethyl 1,3-acetonedicarboxylate (IV) to form a solution of the hydroxyenamine (V), which is then treated, preferably in situ, in a suitable organic solvent (aprotic solvents such as acetonitrile, dichloromethane, etc. are exemplified), under anhydrous conditions, with a 2-haloacetaldehyde at elevated temperatures to produce the N-(2-hydroxyethyl)pyrrole (VI). Compound VI is esterified with methanesulfonyl chloride to produce the mesylate (VII), which is optionally converted to the N-(2-iodoethyl)pyrrole (VIII) by reaction with sodium iodide. Either of compounds VII and VIII may be converted to dimethyl 2,3-dihydro-1H-pyrrolo[1,2-a]pyrrole-1,7-dicarboxylate (II, R=CH₃) by treatment with sodium hydride in dimethylformamide. The thus-formed dimethyl 2,3-dihydro-1H-pyrrolo[1,2-a]-pyrrole-1,7-dicarboxylate may then be selectively 7-decarboxylated and 5-aroylated, by methods such as those described in the previously-cited patents and in U.S. Pat. No. 4,496,741 to Doherty, to yield a 5-aroyl-2,3-dihydro-1H-pyrrolo[1,2-a]pyrrole-1-carboxylic acid (I). A similar process, involving the reaction of ethanolamine, dimethyl 1,3-acetonedicarboxylate, and a halomethyl alkyl ketone, bypasses the hydroxyenamine (V) and produces the 4-alkyl analog of (VI) directly. That compound may be converted to the pyrrolo-pyrrole in the same manner as for the 4-unsubstituted compound previously described.

Processes for the preparation of 5-aroyl-N-R-pyrrole-2-acetic acid, where R is H, lower alkyl, or benzyl, and analogous compounds are disclosed in U.S. Pat. Nos. 3,752,826; 3,865,840; and 3,952,012 to Carson. They include, for the 4-alkyl substituted but not for the 4-unsubstituted compounds, the reaction between a lower alkylamine, a di(lower alkyl) 1,3-acetonedicarboxylate, and a chloromethyl lower alkyl ketone, "preferably in an aqueous medium", followed by pouring into ice-cold hydrochloric acid, to produce compounds of formula IX, where each of R, R', and R" is lower alkyl.

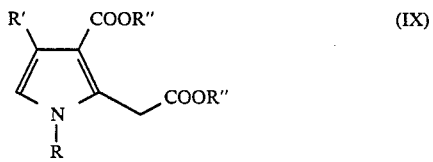

A similar process for the 4-unsubstituted compounds (IX, R'=H) using chloroacetaldehyde is disclosed in U.S. Pat. No. 4,048,191 to Carson.

U.K. Published Application No. 2 034 304 A, assigned to Mallinckrodt, Inc., discloses a process for the preparation of compounds of formula IX, wherein R' may be hydrogen or alkyl, by either (a) forming a two-phase reaction medium of an aqueous solution of the alkylamine and an inert, water-immiscible organic solvent, and adding the dicarboxylate and ketone (or aldehyde) substantially simultaneously, or (b) adding the dicarboxylate and ketone substantially simultaneously, with the ketone in excess, to an aqueous alkylamine. Preferably, dicarboxylate and excess ketone are added to an alkylamine dispersion.

A number of patents assigned to Ethyl Corporation, including U.S. Pat. Nos. 4,565,878; 4,565,879; 4,374,255; 4,388,468; 4,383,117; 4,455,433; and 4,333,878, disclose other modifications of the Carson syntheses. U.S. Pat. No. 4,565,878 discloses the addition of a water-immiscible co-solvent [a halogenated hydrocarbon of good solubility for both the di(lower alkyl) 1,3-acetonedicarboxylate and the product] to the mixture of chloromethyl lower alkyl ketone, dicarboxylate, and aqueous lower alkylamine. U.S. Pat. No. 4,565,789 discloses the use of an aromatic hydrocarbon as the co-solvent. U.S. Pat. No. 4,374,255 discloses the addition of "a solids formation inhibiting amount of a lower alkanol" to the ketone/dicarboxylate/-aqueous alkylamine mixture. The reaction is normally carried out in the presence of a co-solvent as in U.S. Pat. Nos. 4,565,878 or 4,565,879. U.S. Pat. No. 4,388,468 discloses a two-stage process in which (a) the ketone is added to a pre-mixed cooled solution of the alkylamine and the dicarboxylate in a suitable solvent (e.g. aromatic hydrocarbons, chlorinated hydrocarbons, water, or mixtures thereof) at a temperature less than 60° C., followed by (b) heating the reaction mixture to 70°–100° C. U.S. Pat. No. 4,383,117 discloses the use of an anhydrous lower alkylamine instead of an aqueous solution, and the use of a single-phase non-aqueous reaction medium. U.S. Pat. No. 4,455,433 discloses the addition of "a yield-enhancing amount of an acid having a dissociation constant of at least $1.3 \times 10^{-5}$ at 25° C." to a ketone/dicarboxylate/(-preferably anhydrous) lower alkylamine mixture, preferably in an organic solvent. U.S. Pat. No. 4,333,878 discloses the synthesis of compounds of formula IX by the reaction of an enamine (X)

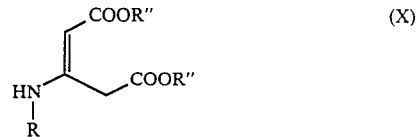

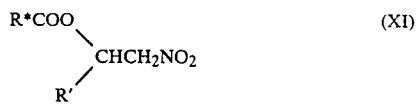

with a 2-carboxy-1-nitroalkane (XI, R*=lower alkyl, tolyl, or benzyl). The enamine may be prepared by the reaction of a di(lower alkyl) 1,3-acetonedicarboxylate with a lower alkylamine in "a suitable solvent, such as ethanol or methanol", followed by evaporation of the solvent and heating to dehydrate the thus-formed carbinolamine to the corresponding enamine.

Albert et al., in U.S. Pat. No. 4,363,918, disclose the synthesis of compounds of formula IX where R is lower alkyl, R' is hydrogen or lower alkyl, and R" is H by the reaction of 1,3-acetonedicarboxylic acid with ClCH$_2$COR and a lower alkylamine, preferably by the slow addition of an aqueous solution of the lower alkylamine to an aqueous solution of the acid, followed by slow addition of the 1-chloro-2-alkanone, with both additions preferably occurring below 20° C. or lower.

European Published Applications Nos. 92 487 and 105 664, assigned to Montedison S.p.A., disclose the preparation of compounds of formula IX wherein R is CH$_3$ and R" is H, and R' is CH$_3$ (EP92487) or H (EP105664) by the reaction of 1,3-acetonedicarboxylic acid or an alkali metal salt thereof with methylamine and a halo (ketone or aldehyde) in aqueous solution, preferably by adding the haloketone to an aqueous mixture of the methylamine and the dicarboxylic acid.

SUMMARY OF THE INVENTION

In a first aspect, this invention relates to the preparation of 2,3-dihydro-1H-pyrrolo[1,2-a]pyrrole-1,7-dicarboxylates of formula XII,

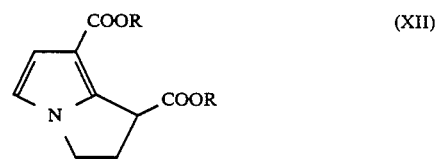

in which
each R is independently H or lower alkyl, from di(-lower alkyl) 1,3-acetonedicarboxylates.

The preparation may be represented schematically:

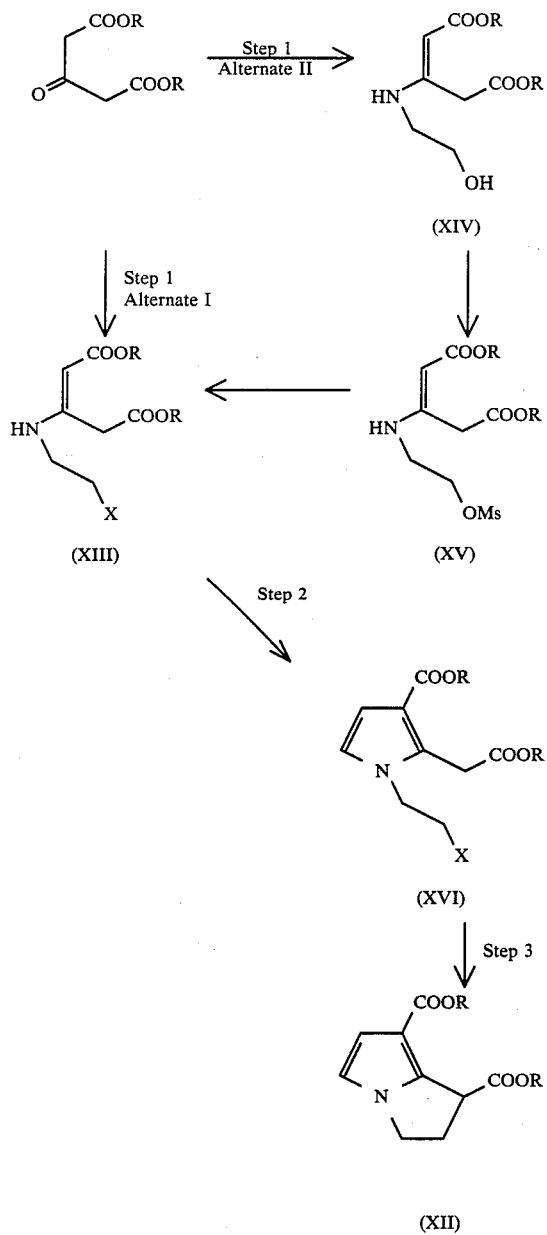

in which
R is as previously defined;
Ms is mesyl; and
X is halogen.

In a second aspect, this invention relates to novel compounds of formulae XIII and XV, which are useful as intermediates in the process herein.

DETAILED DESCRIPTION OF THE INVENTION

Definitions

Unless otherwise stated, the following terms used in the specification and claims have the meanings given below:

"lower alkyl", denoted generally by R (which may also denote hydrogen, although that is not "lower alkyl"), refers to straight, branched, or cyclic saturated hydrocarbon radicals having from one to six carbon atoms, e.g. methyl, ethyl, isopropyl, cyclopropylmethyl, pentyl, cyclohexyl, and the like. Preferred lower alkyls are methyl, ethyl, and n-propyl, and a particularly preferred lower alkyl is methyl. If more than one alkyl radical is present in a given molecule, each may be independently selected from "lower alkyl" unless otherwise stated.

"lower alkoxide", "lower alkanol", "lower alkylamine", "lower alkyl ester", and similar terms refer to alkoxides, alkanols, alkylamines, alkyl esters, etc. in which the (or each) alkyl radical is a "lower alkyl" as defined above.

"halogen", denoted generally by X, refers to chlorine, bromine, or iodine. Preferred halogens are chlorine and bromine.

"aprotic polar solvent" includes organic solvents which may be either water-immiscible, such as halogenated hydrocarbons, e.g. methylene chloride, chloroform, etc., or water-miscible, such as tetrahydrofuran, dimethoxyethane, bis(2-methoxyethyl) ether (diglyme), dimethylformamide, N-methylpyrrolidone, dimethylsulfoxide, etc. The solvent may also contain minor proportions of aprotic non-polar solvents such as hydrocarbons, e.g. cyclohexane, toluene, and the like, provided that the solvent properties are largely determined by the polar solvent.

"weak base" refers to the alkali metal or alkaline earth salt of a weak acid, e.g. sodium acetate, potassium bicarbonate, etc., or to a buffer mixture (such as $NaH_2PO_4/Na_2HPO_4$) giving a similar pH.

"strong base" refers to bases such as alkali metal hydroxides, lower alkoxides, hydrides, di(lower alkyl)-amines, and the like, e.g. sodium hydroxide, potassium methoxide, sodium hydride, lithium di(isopropyl)amine, lithium bis(trimethylsilyl)amine, etc.

"mesyl", denoted by Ms, refers particularly to methanesulfonyl, but includes other equivalent alkyl- or arylsulfonyls, such as ethanesulfonyl, benzenesulfonyl, p-toluenesulfonyl, and the like.

"water-miscible co-solvent" includes lower alkanols, di(lower alkyl) ketones, tetrahydrofuran, dioxane, sulfolane, dimethylformamide, and the like. Preferred co-solvents are methanol, acetone, and similar $C_1$ or $C_2$ alkyl alcohols and ketones.

Starting Materials and Purification

Dimethyl 1,3-acetonedicarboxylate is commercially available (Aldrich), as is 1,3-acetonedicarboxylic acid, also known as 3-oxopentanedioic acid. Other di(lower alkyl) 1,3-acetonedicarboxylates may readily be prepared from either the dimethyl ester or, preferably, the diacid, by esterification techniques well-known to the art. However, there is no particular advantage in varying the alkyl groups, so that the dimethyl ester ($R=CH_3$) is preferred.

The starting materials and the intermediates of formulae XIII, XIV, XV, and XVI may be isolated, if desired, using conventional techniques, including but not limited to filtration, distillation, crystallization, chromatography and the like. Such materials may be characterized using conventional means, including physical constants and spectral data.

Preparation of Compounds of Formula XII

In Step 1, a di(lower alkyl) 3-(2-haloethylamino)-2-pentenedioate ("haloenamine") is prepared from a di(lower alkyl) 1,3-acetonedicarboxylate, either by direct reaction with a 2-haloethylamine hydrohalide salt, or by reaction with 2-hydroxyethylamine (2-aminoethanol) followed by replacement of the hydroxy group by a halide.

In Alternate I (which is preferred), the di(lower alkyl) 1,3-acetonedicarboxylate is treated with a 2-haloethylamine hydrohalide salt in aqueous solution. The solution preferably has a pH between 5 and 12, more preferably between 5 and 8. Typically, the pH is controlled by employing an aqueous solution of a weak base, such as sodium acetate, as the reaction solvent, but other pH control methods may be employed, if desired. The reactants may be added simultaneously or consecutively, as desired, but it is desirable that the 2-haloethylamine hydrohalide not be placed in basic solution unless that solution already contains the acetonedicarboxylate, to avoid the formation of aziridines. Typically, the 2-haloethylamine hydrohalide and acetonedicarboxylate are dissolved, either simultaneously or in the order stated, in water, and a solid weak base added to produce the reaction mixture. The reaction is preferably conducted at a temperature between 0° and 35° C., more preferably at about room temperature, i.e. between about 20° and 30° C.; over a time preferably between about 30 minutes and 24 hours, more preferably between about 4 and 18 hours. The intermediate haloenamine typically crystallizes and may be isolated by filtration, as a mixture of the $\underline{E}$ and $\underline{Z}$ isomers. Each R is preferably methyl, X is preferably Br or Cl, and sodium acetate is preferably used to control pH.

In Alternate II, the di(lower alkyl) 1,3-acetonedicarboxylate is treated with 2-hydroxyethylamine (2-aminoethanol) in an aprotic polar solvent to produce the hydroxyenamine (XIV). Typically, the dicarboxylate is dissolved in the solvent, the 2-hydroxyethylamine is added slowly to the resulting solution, and the water formed during the reaction is removed by azeotropic distillation. While the hydroxyenamine may be formed under less stringent conditions (see, e.g., U.S. Pat. No. 4,089,969), an anhydrous solution of the hydroxyenamine is required for the next reaction, and it is therefore convenient to carry out the formation of the hydroxyenamine in an aprotic medium. The resulting solution contains a mixture of the $\underline{E}$ and $\underline{Z}$ isomers of the hydroxyenamine, and may be used without purification in the next step. As in Alternate I, a preferred R is methyl. A preferred solvent is dichloromethane.

Esterification of the hydroxyenamine (XIV) with mesyl chloride in the presence of an organic base such as a tertiary amine, optionally in the presence of an aprotic polar solvent, takes place at a temperature between about $-10°$ C. and room temperature, preferably between about 0° and 10° C. Conveniently, the tertiary amine is added to the solution from the previous reaction, which has been cooled to the appropriate temperature, and the mesyl chloride is added slowly to the resulting solution over a period between about 30 minutes and 10 hours, typically about 2 to 5 hours. The solution of the resulting mesylenamine (XV) is quenched with water, and solvent removed from the organic phase to afford a mixture of the $\underline{E}$ and $\underline{Z}$ isomers of the mesylenamine (XV), which may be used without further purification in the next reaction.

The mesylenamine (XV) is converted into the corresponding haloenamine (XIII) by reaction with an anhydrous alkali halide, preferably a bromide or iodide, e.g. sodium iodide, lithium bromide, etc., in an aprotic polar solvent at a temperature between about room temperature and the reflux temperature of the solvent, e.g. between about 30° and 100° C., for 1 to 30 hours, e.g. between 5 and 20 hours, the period depending on the reagents and reaction temperature. The haloenamine (XIII) may be readily isolated by adding water to the reaction mixture, washing the organic phase, and removing the solvent to afford a mixture of the $\underline{E}$ and $\underline{Z}$ isomers of the haloenamine, which may conveniently be purified by recrystallization.

Preparation of Compounds of Formula XII

In Step 2, the haloenamine (XIII) is treated with a 2-haloacetaldehyde, $XCH_2CHO$, wherein X is as defined above. The process is preferably conducted in aqueous solution at a pH between 4.5 and 10, preferably between 5 and 8.5. The reaction is preferably carried out between 0° and 65° C., more preferably at about room temperature, for from about 1 to 48 hours, preferably between 6 and 24 hours. X is preferably Br, and pH control is preferably achieved by the presence of a weak base, e.g. sodium acetate or sodium bicarbonate, in the solution. The process is preferably conducted in the presence of 10 to 50 volume percent of a water-miscible co-solvent, such as acetone.

To an aqueous solution of a weak base and the 2-haloacetaldehyde is added the haloenamine (XIII). A water-miscible co-solvent is preferably also added. The mixture is stirred for the appropriate time, and the $\underline{N}$-(2-haloethyl)-pyrrole (XVI) is isolated by filtration. The 2-haloacetaldehyde may be obtained commercially or prepared by any desired route. In the case of the preferred 2-bromoacetaldehyde, exemplary preparative methods include the acid hydrolysis of a 2-bromoacetaldehyde di(lower alkyl) acetal, a lower alkyl 1,2-dibromoethyl ether, 1,2-dibromoethyl acetate, etc., each of which results in an aqueous solution of 2-bromoacetaldehyde, to which may be added the weak base.

Finally, in Step 3, the $\underline{N}$-(2haloethyl)pyrrole (XVI) is cyclized with from 1 to $\overline{2}$ equivalents, preferably about 1.1 to 1.5 equivalents, of a strong base in an aprotic polar solvent. The process may further include the saponification of the diester to the dicarboxylic acid (XII, R=H), which may conveniently be performed on the solution of the diester from the cyclization process.

A preferred X is Br or Cl. The strong base is preferably a lithium hindered amine, such as lithium di(isopropyl)amine or lithium bis(trimethylsilyl)amine; and the solvent, tetrahydrofuran. Other suitable exemplary strong base/solvent combinations include sodium hydroxide in dimethylsulfoxide and potassium methoxide in methanol (although this latter tends to give an increased quantity of the $\underline{N}$-vinylpyrrole impurity). The use of sodium hydride in dimethylformamide for the cyclization of the $\underline{N}$-(2-iodoethyl)pyrrole is known from, e.g., U.S. Pat. $\overline{N}$o. 4,089,969.

The compound of formula XVI is dissolved in the aprotic polar solvent, and a solution of the strong base is added slowly (i.e. over a period of from about 1 to 24 hours, e.g. about 2 to 8 hours) at a temperature of about $-10°-35°$ C., e.g. at room temperature, and the resulting solution is stirred to afford a solution of the pyrrolopyrrole diester (XII). The reaction temperature is preferably 0°–10° C. for X=Br, and 15°–30° C. for X=Cl, when the strong base is lithium di(isopropyl)amine. Compound (XII) may be recovered from the solution by removal of the solvent and purification by conventional organic chemical means, or, more usually, may be converted directly to the dicarboxylic acid (XII, R=H).

If the dicarboxylic acid, (XII, R=H), is desired, the diester may be saponified by conventional chemical means, i.e. reaction with a strong base to remove the ester groups and treatment with acid to generate the dicarboxylic acid. The saponification may be performed on isolated material; but may conveniently be performed on the solution produced in the cyclization reaction described above. For example, water may be added to the solution, the aprotic polar solvent at least partially removed by distillation, and a strong base, e.g. sodium hydroxide, may be added directly to the resulting solution of the pyrrolo-pyrrole diester, the solvent further partially removed (if desired or necessary), and an aqueous strong acid, e.g. 35% hydrochloric acid, added. The dicarboxylic acid precipitates from the solution, and may be removed by filtration. The dicarboxylic acid may be purified by conventional chemical means, especially conveniently by recrystallization from aqueous solution.

The C-1 acid group of the resulting dicarboxylic acid (XII, R=H) may then be selectively esterified, and the 1-ester-7-acid decarboxylated to afford the pyrrolo-pyrrole-1-carboxylate, which may be 5-aroylated to afford compounds of formula I, all by methods described in the patents set forth in the "Background to the Invention" section of this application, e.g. U.S. Pat. No. 4,089,969.

EXAMPLES

The following Examples illustrate this invention, but are not intended to limit its scope.

Example 1

Preparation of dimethyl 3-(2-bromoethylamino)-2-pentenedioate. (Step 1—Alternate I)

A. 2-Bromoethylamine hydrobromide (12.35 g, 60 mmol) was dissolved in water (30 mL) at room temperature (20° C.) with stirring, and dimethyl 1,3-acetonedicarboxylate (10.0 g, 57 mmol) was added. After 5-10 minutes, solid anhydrous sodium acetate (14.35 g, 175 mmol) was added, and stirring continued. After approximately 80 minutes, precipitation of dimethyl 3-(2-bromoethylamino)-2-pentenedioate began, and the solution was stirred for 17 hours at room temperature. The thick slurry was diluted with cold water (20 mL), and aged at 0°-5° C. for 30 minutes and filtered, and the precipitate washed with cold (0°-5° C.) water (50 mL) and dried to constant weight, to afford 13.9 g (86% yield) of dimethyl 3-(2-bromoethylamino)-2-pentenedioate as a white solid, m.p. 71°-72° C., NMR (CDCl$_3$): δ:

8.80 (1H, broad singlet)
4.60 (1H, singlet)
3.85 (3H, singlet)
3.77 (3H, singlet)
3.35-3.72 (4H, broad multiplet)
3.25 (2H, singlet).

B. Substituting 2-chloroethylamine hydrochloride (7.0 g, 60 mmol) for the 2-bromoethylamine hydrobromide in the procedure of part A of this Example, there was obtained 10.8 g (80% yield) of dimethyl 3-(2-chloroethylamino)-2-pentenedioate as a white solid, m.p. 75°-76° C., NMR (CDCl$_3$): δ:

8.80 (1H, broad singlet)
4.60 (1H, singlet)
3.75 (3H, singlet)
3.65 (3H, singlet)
3.60 (4H, multiplet)
3.27 (2H, singlet).

C. Substituting for dimethyl 1,3-acetonedicarboxylate in the procedure of parts A or B of this Example,
 diethyl 1,3-acetonedicarboxylate,
 dipropyl 1,3-acetonedicarboxylate,
 di(i-propyl) 1,3-acetonedicarboxylate,
 di(t-butyl) 1,3-acetonedicarboxylate, or
 dihexyl 1,3-acetonedicarboxylate,
one obtains, respectively,
 diethyl 3-(2-bromoethylamino)-2-pentenedioate,
 dipropyl 3-(2-bromoethylamino)-2-pentenedioate,
 di(i-propyl) 3-(2-bromoethylamino)2-pentenedioate,
 di(t-butyl) 3-(2-bromoethylamino)-2-pentenedioate,
 dihexyl 3-(2-bromoethylamino)-2-pentenedioate,
 diethyl 3-(2-chloroethylamino)-2-pentenedioate,
 dipropyl 3-(2-chloroethylamino)-2-pentenedioate,
 di(i-propyl) 3-(2-chloroethylamino)2-pentenedioate,
 di(t-butyl) 3-(2-chloroethylamino)2-pentenedioate, or
 dihexyl 3-(2-chloroethylamino)-2-pentenedioate.

Example 2

Preparation of dimethyl 3-(2-bromoethylamino)-2-pentenedioate. (Step 1—Alternate II)

A. Dimethyl 1,3-acetonedicarboxylate (196.1 g, 1.13 mol) was placed in a 3 L three-neck flask containing a stirrer bar and fitted with a thermometer, a water extractor on a reflux condenser, and an addition funnel; and the flask then purged with nitrogen. The extractor was filled with dichloromethane, and dichloromethane (800 mL) added to the flask. Ethanolamine (68.8 g, 1.13 mol) was added via the addition funnel over 10 minutes, and the mixture warmed to 30° C. The mixture was then heated under reflux for 24 hours, by which time thin-layer chromatography indicated that very little residual dicarboxylate remained and 20 mL water had collected in the extractor.

The solution of dimethyl 3-(2-hydroxyethylamino)-2-pentenedioate was cooled to 0° C., and triethylamine (235 mL, 170.6 g, 1.69 mol) was added in one portion. Methanesulfonyl chloride (168.8 g, 1.47 mol) was added dropwise via an addition funnel over 3.75 hours, with the temperature rising to 5°-7° C. The medium-yellow slurry darkened to yellow-orange as the last 10 mL methanesulfonyl chloride was added. The mixture was stirred at 0° C. for an additional 2 hours, and water (250 mL) added. The organic phase was washed with water (4×500 mL) and brine (250 mL), and dried overnight over anhydrous magnesium sulfate. After filtration, the solvents were evaporated on a rotary evaporator under reduced pressure at 50° C. to afford 310.0 g (93% yield) of dimethyl 3-(2-methanesulfonylethylamino)-2-pentenedioate as a red oil.

Dimethyl 3-(2-methanesulfonylethylamino)-2-pentenedioate (156.3 g, 529 mmol) was added to a 2 L three-neck flask, which was fitted with a mechanical stirrer, thermometer, and reflux condenser. Dichloromethane (750 mL) was added and stirred until the mesylate had completely dissolved, anhydrous lithium bromide (69.0 g, 794 mmol) was added, and the mixture stirred at 35° C. for 19 hours. The mixture was cooled to 0° C. and water (250 mL) added, then stirred for 5 minutes and the phases separated. The organic phase was washed with water (3×250 mL) and brine (150 mL), and dried over anhydrous potassium carbonate for 15 minutes. Rotary evaporation of the solvent under reduced pressure (50° C.) gave 128.4 g of crude dimethyl 3-(2-bromoethylamino)-2-pentenedioate as a yellow oil, which quickly solidified to a yellow solid. The crude material was purified by extraction into boiling hexane (5×750 mL) and recrystallization from hexane, and the pot residues extracted and recrystallized, to give a total of 90.8 g (61.2% yield) of dimethyl 3-(2-bromoethylamino)-2-pentenedioate as white needles. An NMR spectrum in CDCl$_3$ indicated an Z/E isomer ratio of 19:1, and remeasurement of the CDCl$_3$ solution after three days indicated an Z/E ratio of 4:1. The two isomers were not separated.

B. In a similar manner to that of part A of this Example, using sodium iodide in place of lithium bromide, and acetone or acetonitrile in place of dichloromethane, there was obtained in each instance crude dimethyl 3-(2-iodoethylamino)-2-pentenedioate as a light brown oil, which could be purified by conventional methods.

C. Substituting lithium chloride for lithium bromide, and using a similar procedure to that in part A of this Example, one obtains dimethyl 3-(2-chloroethylamino)-2-pentenedioate.

D. Similarly, using other di(lower alkyl) 1,3-acetonedicarboxylates in the procedures of parts A through C of this Example, one obtains other di(lower alkyl) 3-(2-haloethylamino)-2-pentenedioates.

Example 3

Preparation of methyl N-(2-bromoethyl)-3-methoxycarbonyl-2-pyrroleacetate. (Step 2)

A. 2-Bromoacetaldehyde diethyl acetal (42.2 g, 214 mmol) was added to a 100 mL three-neck flask fitted with a mechanical stirrer, reflux condenser, and a thermometer. Hydrobromic acid (9M, 4.0 mL, 36 mmol) in water (16 mL) was added, and the mixture heated under reflux for 1 hour and then cooled to room temperature to provide a solution of 2-bromoacetaldehyde.

Sodium acetate (41.0 g, 500 mmol) was added to the 2-bromoacetaldehyde solution, and stirred for 5 minutes, at which point the solution had a pH of 6. The flask was placed in a cool tap water bath and dimethyl 3-(2-bromoethylamino)-2-pentenedioate (20.0 g, 71 mmol) was added, followed by isopropanol (40 mL), and the solution was stirred at room temperature (25° C.). Within about 35 minutes, all the solids had dissolved, and a precipitate started forming within 90 minutes. Stirring was continued at room temperature for 20 hours, and the solution then cooled to 0° C. and stirred at that temperature for 1 hour, then filtered through a coarse frit. The precipitate was washed with ice-cold water (400 mL) and ice-cold isopropanol (150 mL) and dried, to give 15.7 g (72% yield) of crude methyl N-(2-bromoethyl)-3-methoxycarbonyl-2-pyrroleacetate as a light tan solid, m.p. 129°–130.5° C., NMR (CDCl$_3$): δ:

6.58 (2H, quartet)
4.20 (2H, triplet)
4.10 (2H, singlet)
3.75 (3H, singlet)
3.65 (3H, singlet)
3.50 (2H, triplet).

B. 2-Bromoacetaldehyde diethyl acetal (20.9 g, 106 mmol) was added to a 100 mL three-neck flask fitted with a stirrer bar, reflux condenser, and a thermometer. Hydrobromic acid (48.5%, 17.7 g, 106 mmol) in water (54 mL) was added, and the mixture heated to 40° C. for 3 hours and then cooled to room temperature and extracted with hexane (100 mL) to provide a solution of 2-bromoacetaldehyde.

The hydrolysis solution was added to a mechanically-stirred slurry of sodium acetate (17.8 g, 212 mmol) in water (15 mL) at 0° C. over 1 hour, then stirred for a further 10 minutes. Dimethyl 3-(2-chloroethylamino)-2-pentenedioate (20.0 g, 85 mmol) was added, followed by acetone (50 mL), and the solution allowed to warm to room temperature and stirred for 20 hours. The resulting slurry was cooled to 0° C. and kept at that temperature for 4 hours, then filtered through a coarse frit. The precipitate was washed with water (300 mL) and dried, to give 19.9 g (90% yield) of methyl N-(2-chloroethyl)-3-methoxycarbonyl-2-pyrroleacetate as white crystals, m.p. 110°–111° C., NMR (CDCl$_3$): δ:

6.65 (2H, quartet)
4.25 (2H, triplet)
4.18 (2H, singlet)
3.82 (3H, singlet)
3.75 (2H, triplet)
3.73 (3H, singlet).

C. Substituting 2-chloroacetaldehyde diethyl acetal for 2-bromoacetaldehyde diethyl acetal, and using a similar procedure to that in parts A or B of this Example, one obtains methyl N-(2-bromoethyl)-3-methoxycarbonyl-2-pyrroleacetate, or methyl N-(2-chloroethyl)-3-methoxycarbonyl-2-pyrroleacetate.

D. Similarly, substituting other di(lower alkyl) 3-(2-haloethylamino)-2-pentenedioates, such as dimethyl 3-(2-iodoethylamino)-2-pentenedioate, diethyl 3-(2-bromoethylamino)-2-pentenedioate, etc., for the equivalent materials in parts A through C of this Example, one obtains other alkyl N-(2-haloethyl)-3-alkoxycarbonyl-2-pyrroleacetates, such as methyl N-(2-iodoethyl)-3-methoxycarbonyl-2-pyrroleacetate, ethyl N-(2-bromoethyl)-3-ethoxycarbonyl-2-pyrroleacetate, etc.

Example 4

Preparation of dimethyl 2,3-dihydro-1H-pyrrolo[1,2-a]pyrrole-1,7-dicarboxylate and 2,3-dihydro-1H-pyrrolo[1,2-a]pyrrole-1,7-dicarboxylic acid. (Step 3)

A. Under nitrogen, n-butyllithium (1.3M in hexane, 75 mL, 98 mmol) was added slowly at −5°–0° C., with stirring, to a solution of di(isopropyl)amine (13.8 mL, 10.0 g, 98 mmol) in tetrahydrofuran (dry, 50 mL). The resulting solution was transferred to an addition funnel and added, under nitrogen at 0°–5° C., to a stirred slurry of methyl N-(2-bromoethyl)-3-methoxycarbonyl-2-pyrroleacetate (20.0 g, 66 mmol) in tetrahydrofuran (dry, 100 mL). There was a slight temperature rise, and complete dissolution occurred after addition of about two-thirds of the lithium di(isopropyl)amine solution. The resulting solution was stirred for 2 hours while warming to 10° C., then diluted with water (100 mL) with slight heat evolution. The solvents were stripped by atmospheric distillation: 240 mL collected, with a pot temperature of 80° C., to afford a solution of dimethyl 2,3-dihydro-1H-pyrrolo-[1,2-a]pyrrole-1,7-dicarboxylate. The diester may be isolated at this point by quenching with water, extraction into an organic solvent such as ethyl acetate, and evaporation of the solvent; and purified by conventional methods. However, it is also convenient to saponify the diester to the dicarboxylic acid without isolation from the solution.

The pot solution from the previous paragraph was cooled to 50° C. and sodium hydroxide (6.0 g, 150 mmol) added; then methanol was removed by atmospheric distillation to a pot temperature of 97° C. The pot solution was cooled to 5° C. and acidified with hydrochloric acid (12M, 18 mL, 216 mmol), resulting in a temperature rise to 15° C. The resulting mixture was cooled to 5° C. and filtered, and the precipitate washed with cold water (50 mL) and dried, to give 11.4 g of crude 2,3-dihydro-1H-pyrrolo[1,2-a]pyrrole-1,7-dicarboxylic acid. Assay of the crude material indicated that it contained 91.4% 2,3-dihydro-1H-pyrrolo-[1,2-a]pyrrole-1,7-dicarboxylic acid (and 7.0% N-vinyl-3-carboxy-2-pyrroleacetic acid).

B. n-Butyllithium (2.6M in hexane, 295.5 mL, 0.77 mol) was added dropwise at 0°–3° C., with stirring, to a solution of di(isopropyl)amine (109.3 mL, 78.9 g, 0.78 mol) in tetrahydrofuran (freshly distilled, 200 mL). The resulting solution was transferred to an addition funnel and added dropwise at room temperature to a stirred solution of methyl N-(2-chloroethyl)-3-methoxycarbonyl-2-pyrroleacetate (150.0 g, 0.58 mol) in tetrahydrofuran (dry, 750 mL). The addition took 4 hours, and the temperature was maintained in the range of 23°–27° C. The resulting solution was stirred for 16 hours, then diluted with water (500 mL) over 10 minutes with slight heat evolution. The solvents were stripped by atmospheric distillation to a pot temperature of 75° C. The pot solution was cooled to 50° C. and sodium hydroxide (53.0 g, 1.33 mol) added; then methanol was removed by atmospheric distillation to a pot temperature of 95° C.; with a total of 1370 mL of solvents collected. The pot solution was cooled to −3°–0° C. and acidified with hydrochloric acid (12M, 180 mL, 216 mmol), resulting in a temperature rise to 18° C. The resulting mixture was cooled to −3°–0° C., aged for 30 minutes at that temperature, and filtered, and the precipitate washed with ice-cold water (300 mL) and dried, to give 107.8 g of crude 2,3-dihydro-1H-pyrrolo[1,2-a]pyrrole-1,7-dicarboxylic acid. Assay of the crude material indicated that it contained 96.6% 2,3-dihydro-1H-pyrrolo-[1,2-a]pyrrole-1,7-dicarboxylic acid.

C. Similarly, substituting for the methyl N-(2-bromethyl)-3-methoxycarbonyl-2-pyrroleacetate or methyl N-(2-chloroethyl)-3-methoxycarbonyl-2-pyrroleacetate of parts A and B of this Example, methyl N-(2-iodoethyl)-3-methoxycarbonyl-2-pyrroleacetate, ethyl N-(2-chloroethyl)-3-ethoxycarbonyl-2-pyrroleacetate, and similar (lower alkyl) N-(2-haloethyl)-3-(lower alkoxy)carbonyl-2-pyrroleacetates, one obtains dimethyl 2,3-dihydro-1H-pyrrolo[1,2-a]pyrrole-1,7-dicarboxylate or 2,3-dihydro-1H-pyrrolo[1,2-a]pyrrole-1,7-dicarboxylic acid, diethyl 2,3-dihydro-1H-pyrrolo[1,2-a]pyrrole-1,7-dicarboxylic or 2,3-dihydro-1H-pyrrolo[1,2-a]pyrrole-1,7-dicarboxylic acid, and similar di(lower alkyl) 2,3-dihydro-1H-pyrrolo[1,2-a]-pyrrole-1,7-dicarboxylates or 2,3-dihydro-1H-pyrrolo-[1,2-a]pyrrole-1,7-dicarboxylic acids.

We claim:

1. A process for producing a diester of formula XII,

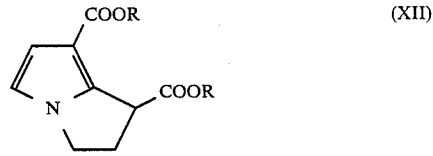

in which each R is independently lower alkyl, which comprises cyclizing a compound of formula XVI,

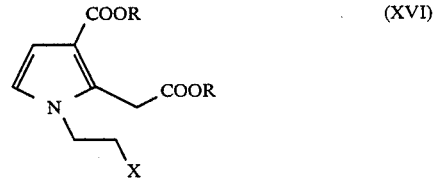

in which

R is as defined above; and

X. is Br or C7, with a lithium hindered amine in an aprotic polar solvent.

2. The process of claim 1 wherein the lithium hindered amine is of the formula $LiNR_2$, in which R is as defined in claim 1.

3. The process of claim 2 wherein $LiNR_2$ is lithium di(isopropyl)amide.

4. The process of claim 1 wherein the aprotic polar solvent is tetrahydrofuran.

5. The process of claim 1 wherein each R is $CH_3$.

6. The process of claim 1 which further includes saponification of the thus-formed diester (XII) to the corresponding diacid (XII, R=H).

7. The process of claim 6 wherein the saponification of the diester (XII) is performed on the solution from the cyclization reaction without isolation of the diester.

* * * * *